(12) United States Patent
Lee

(10) Patent No.: US 12,048,645 B2
(45) Date of Patent: Jul. 30, 2024

(54) MENSTRUAL CUP

(71) Applicant: Ji Soo Lee, Ansan-si (KR)

(72) Inventor: Ji Soo Lee, Ansan-si (KR)

( * ) Notice: Subject to any disclaimer, the term of this patent is extended or adjusted under 35 U.S.C. 154(b) by 0 days.

(21) Appl. No.: 17/628,230

(22) PCT Filed: Nov. 23, 2020

(86) PCT No.: PCT/KR2020/016541
§ 371 (c)(1),
(2) Date: Jan. 19, 2022

(87) PCT Pub. No.: WO2021/107520
PCT Pub. Date: Jun. 3, 2021

(65) Prior Publication Data
US 2024/0033121 A1 Feb. 1, 2024

(30) Foreign Application Priority Data

Nov. 25, 2019 (KR) .................. 10-2019-0151799
Dec. 30, 2019 (KR) .................. 10-2019-0177223
Jan. 16, 2020 (KR) .................. 10-2020-0005765
Nov. 17, 2020 (KR) .................. 10-2020-0153237

(51) Int. Cl.
*A61F 5/455* (2006.01)
*A61F 5/44* (2006.01)

(52) U.S. Cl.
CPC .......... *A61F 5/4553* (2013.01); *A61F 5/4407* (2013.01)

(58) Field of Classification Search
CPC ..... A61F 5/4553; A61F 5/455; A61F 13/2045
See application file for complete search history.

(56) References Cited

U.S. PATENT DOCUMENTS 4,799,929 A * 1/1989 Knowles ............... A61F 5/4553
604/331
5,827,248 A * 10/1998 Crawford ............. A61F 5/4553
604/328
2017/0189222 A1 7/2017 Lin
2017/0360594 A1* 12/2017 Park ........................ A61F 5/449

FOREIGN PATENT DOCUMENTS

| CN | 103705331 A | * | 4/2014 |
| CN | 103705331 B | | 6/2017 |
| GB | 2425260 A | | 10/2006 |
| KR | 10-1848206 B1 | | 5/2018 |
| KR | 10-1897208 B1 | | 10/2018 |

OTHER PUBLICATIONS

International Search Report for PCT/KR2020/016541 mailed Mar. 9, 2021 from Korean Intellectual Property Office.

* cited by examiner

*Primary Examiner* — Susan S Su
*Assistant Examiner* — Meagan Ngo
(74) *Attorney, Agent, or Firm* — Revolution IP, PLLC

(57) ABSTRACT

The present invention relates to a menstrual cup, the menstrual cup according to the present invention comprising: a main body having an open end and a space therein in which menstrual blood is collected; an outlet on the other end of the main body; a stopper packing for blocking the outlet; and a connection part which has one end thereof connected to the stopper packing and the other end thereof directly or indirectly connected to the main body, and which is made of an elastic material so as to move the stopper packing to the original position thereof, if the stopper packing has been spaced away from the outlet due to an external force and then the external force is removed.

10 Claims, 19 Drawing Sheets

[FIG 1]
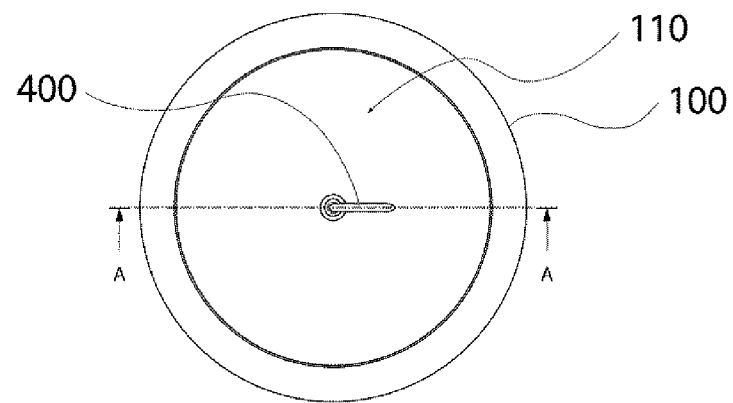
[FIG 2]
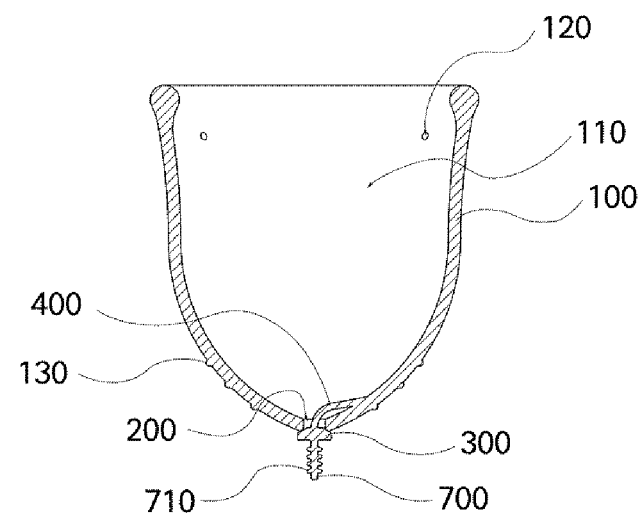

[FIG 3]
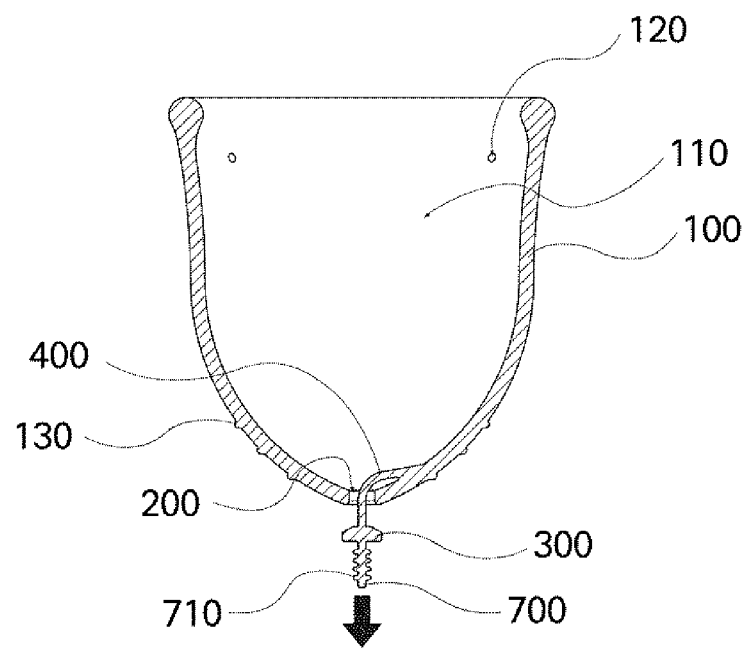
[FIG 4]
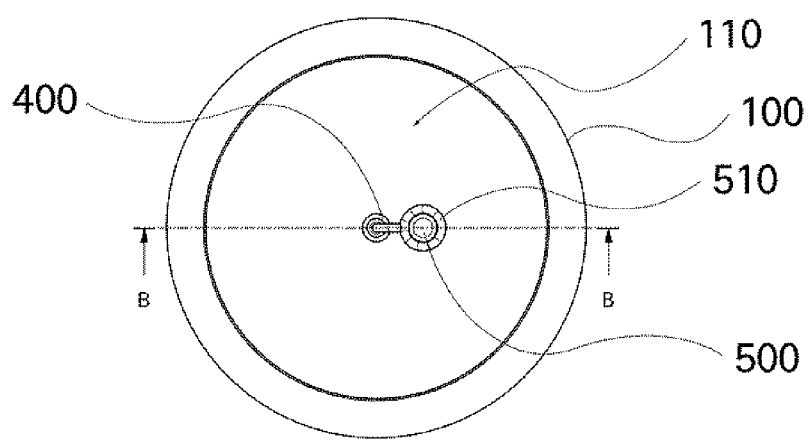

[FIG 5]
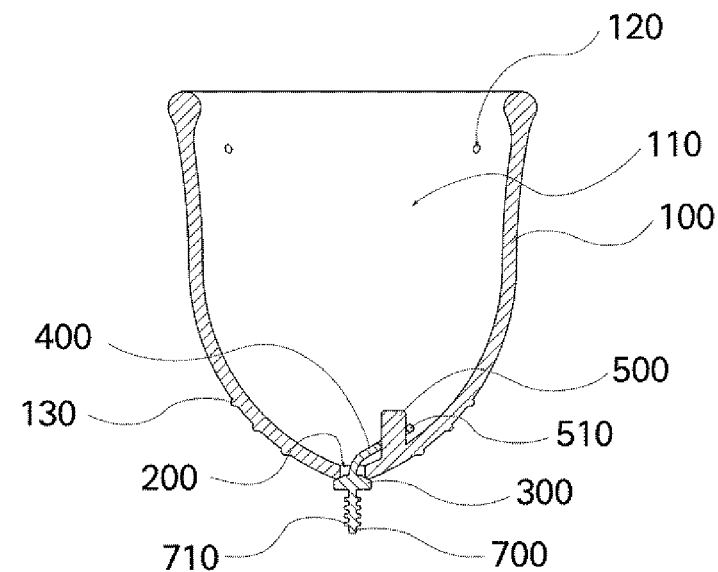
[FIG 6]
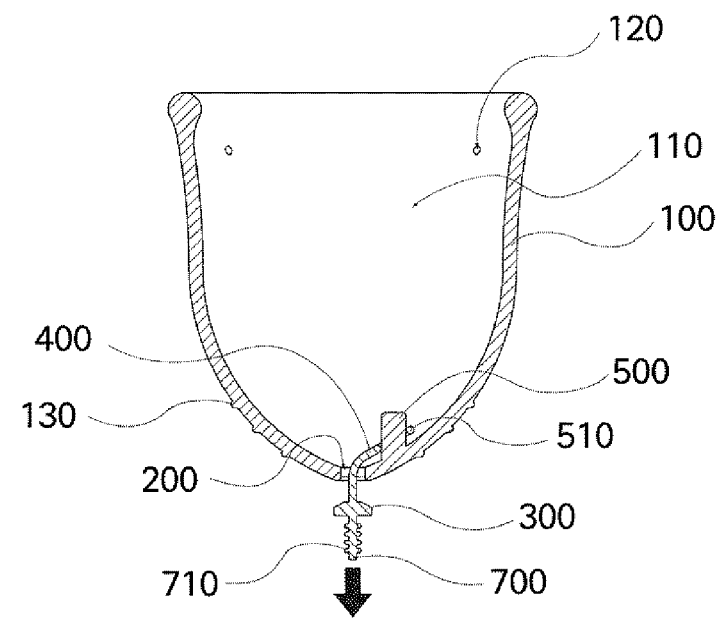

[FIG 7]
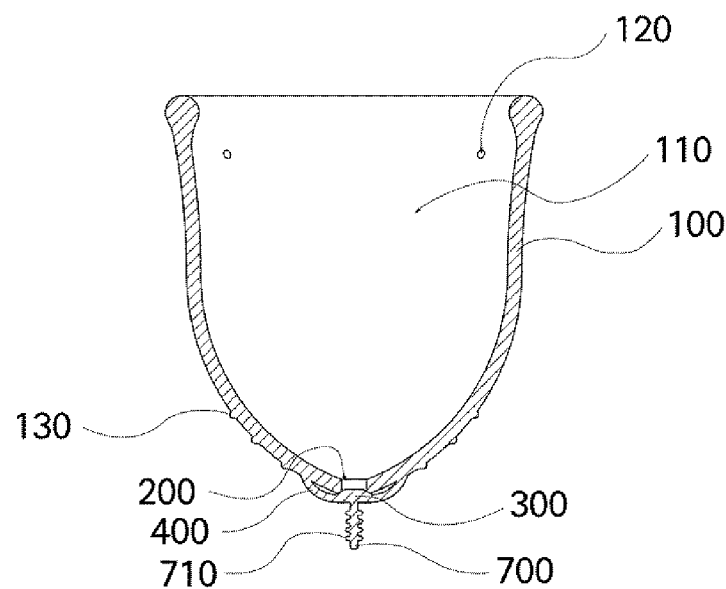
[FIG 8]
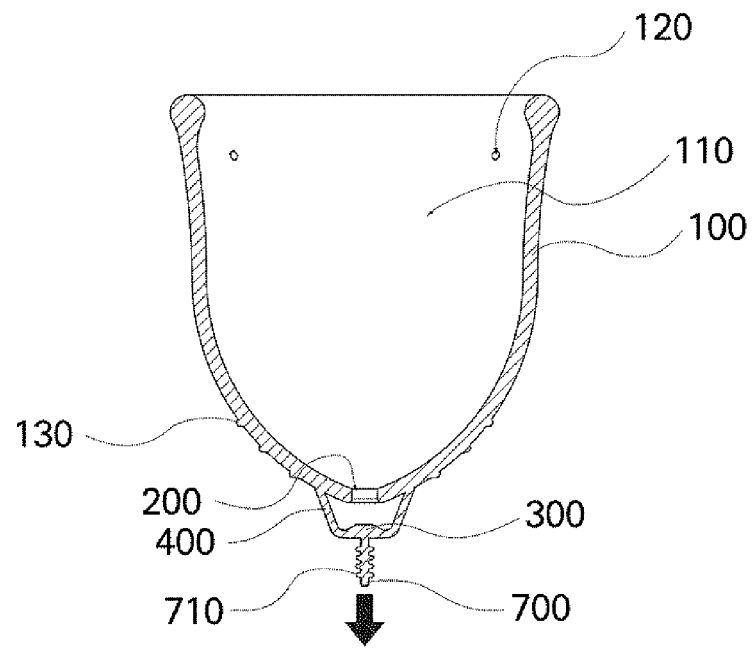

[FIG 9]
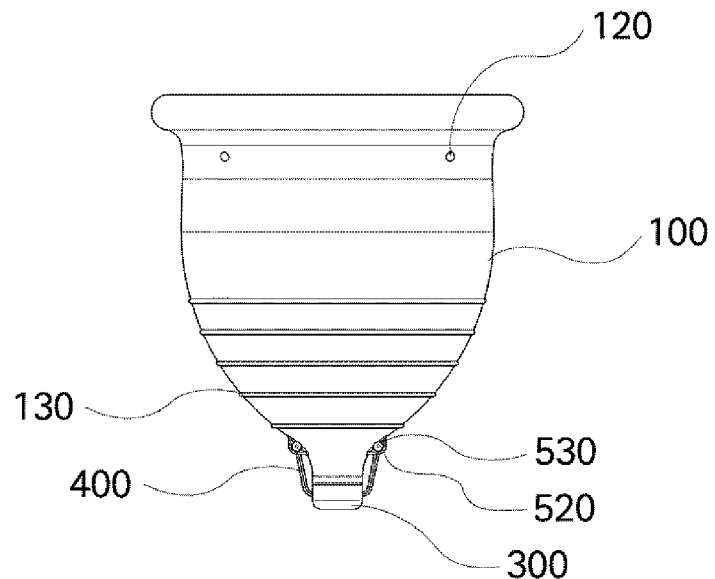
[FIG 10]
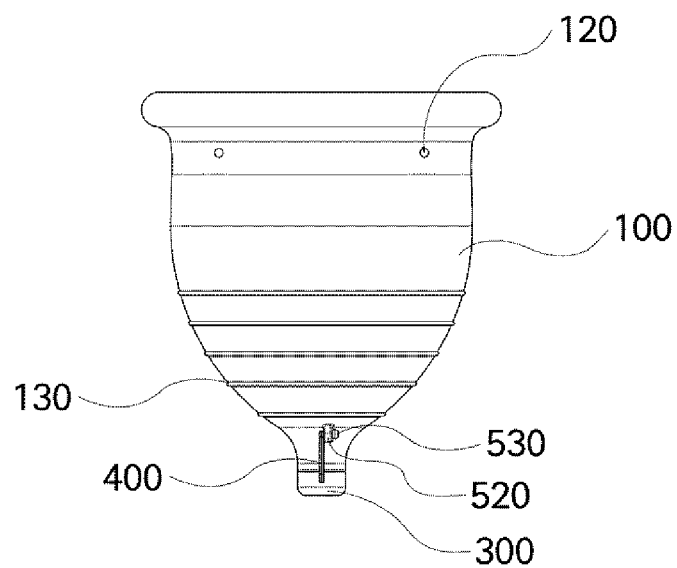

[FIG 11]
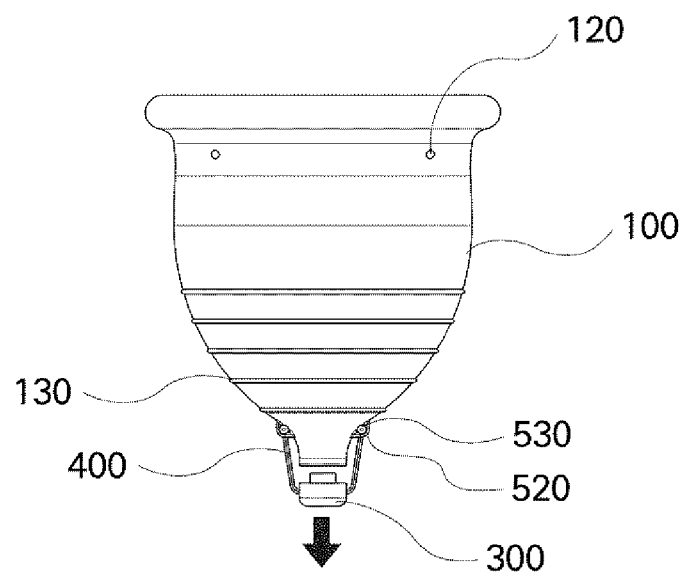
[FIG 12]
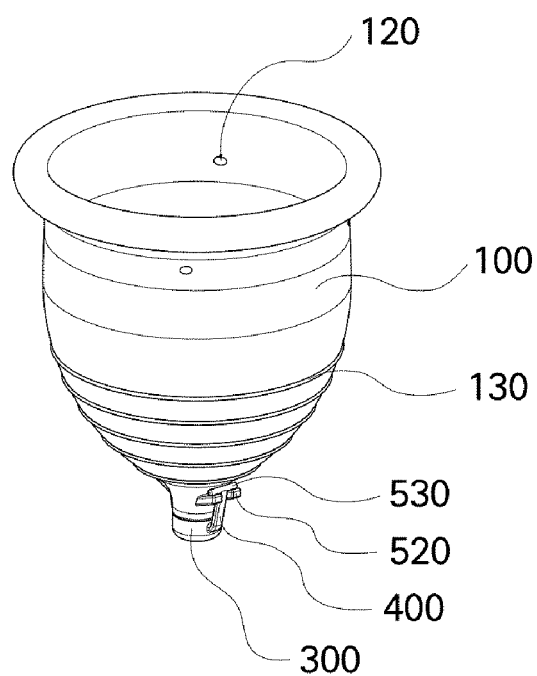

[FIG 13]
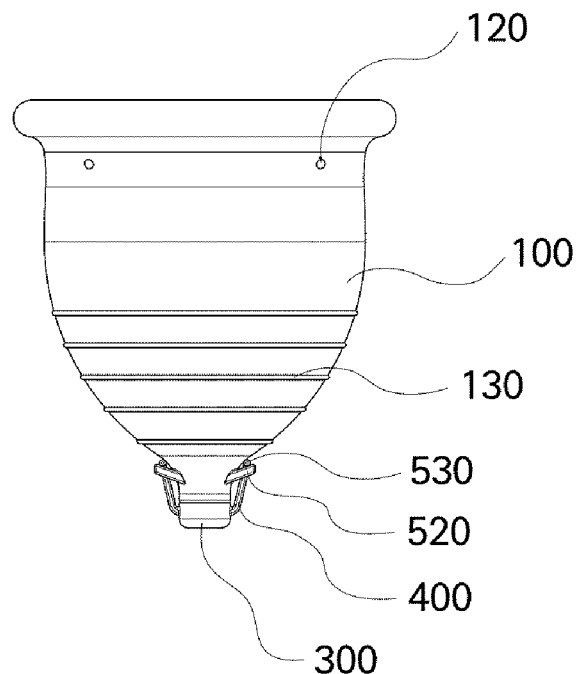
[FIG 14]
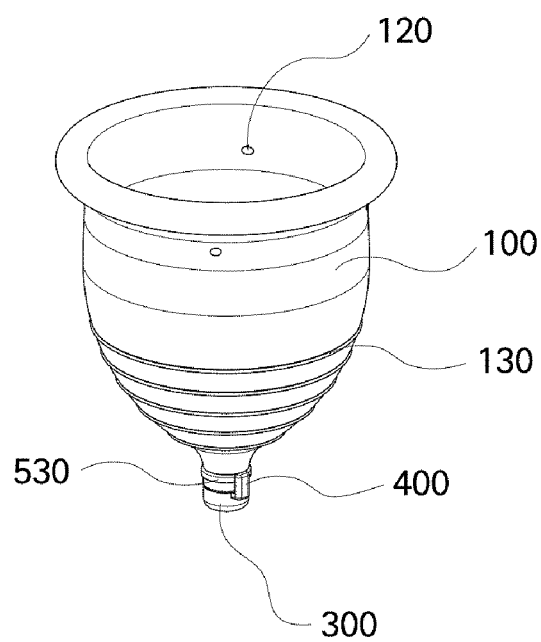

[FIG 15]
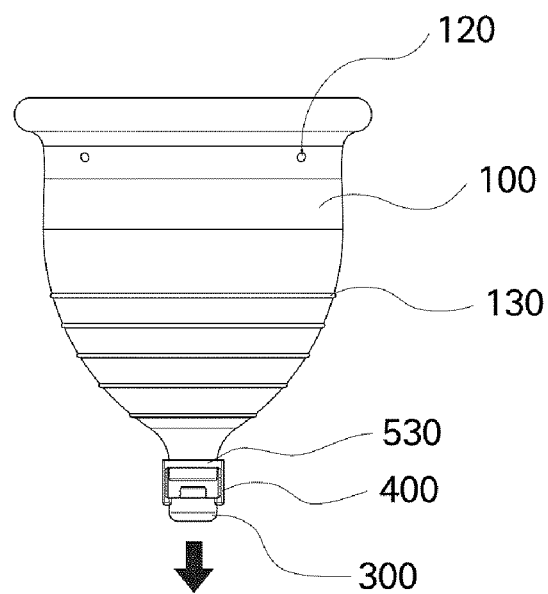
[FIG 16]
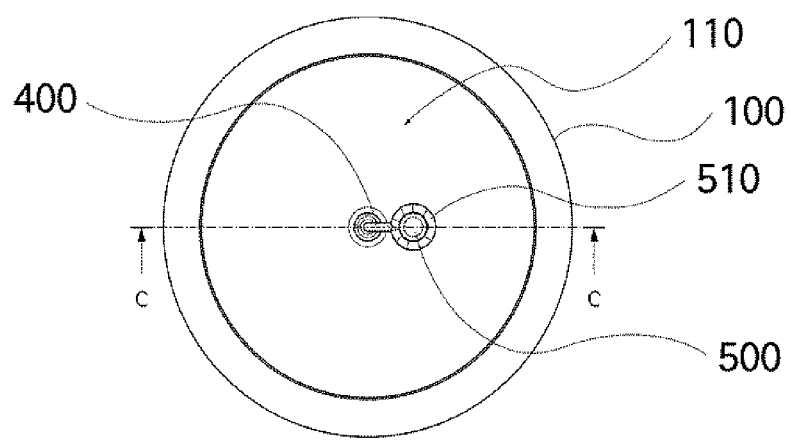

[FIG 17]
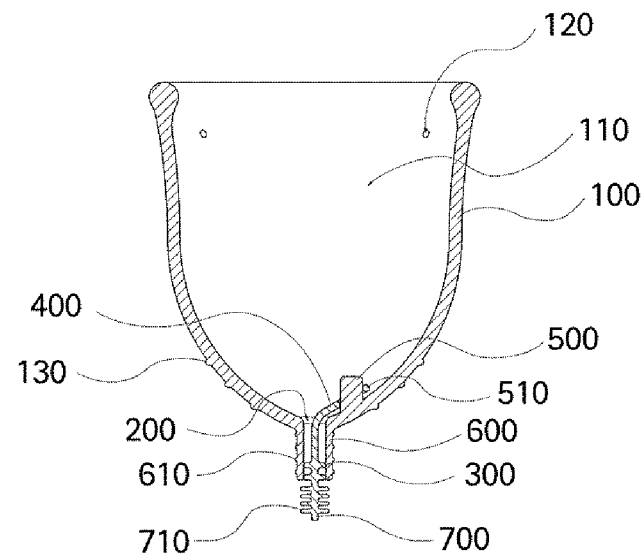
[FIG 18]
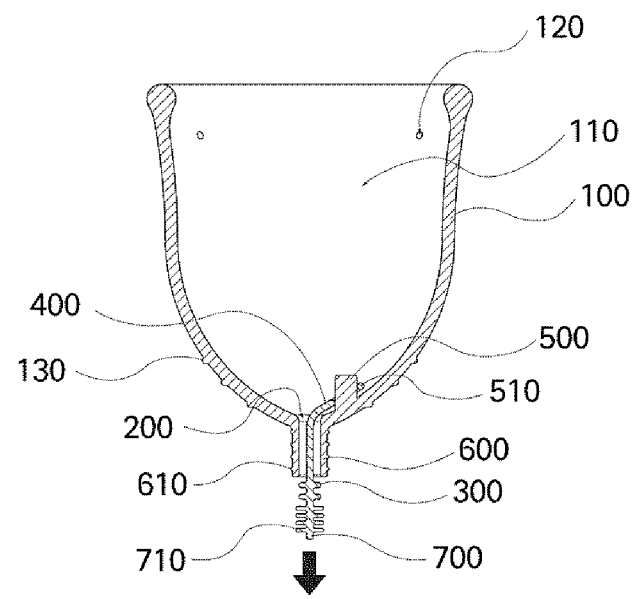

[FIG 19]
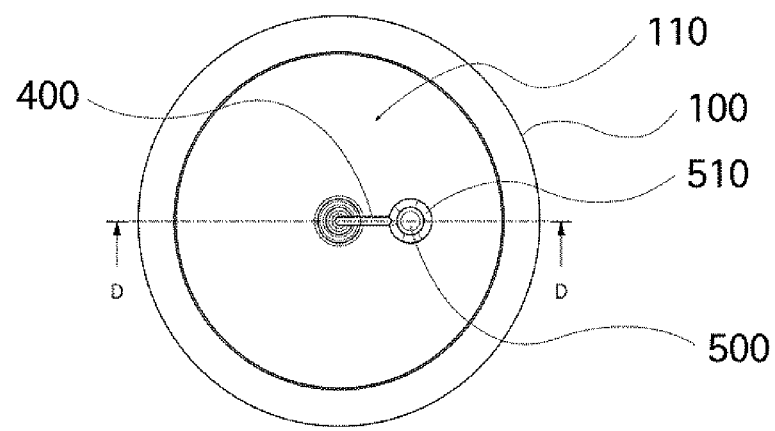
[FIG 20]
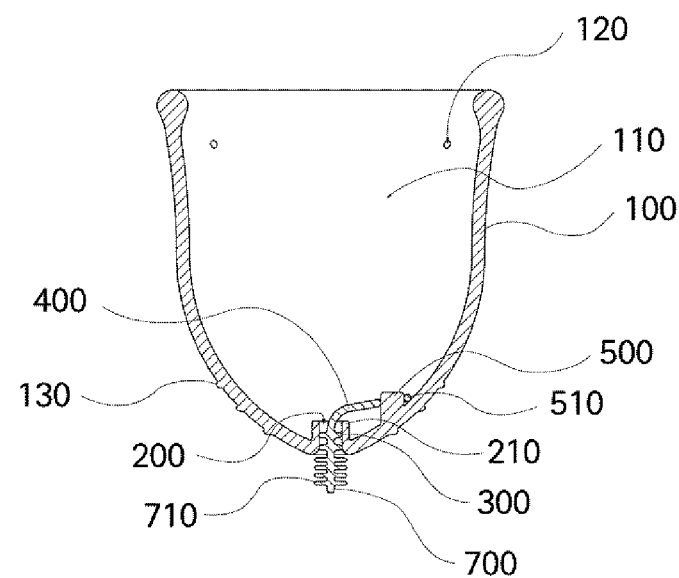

[FIG 21]
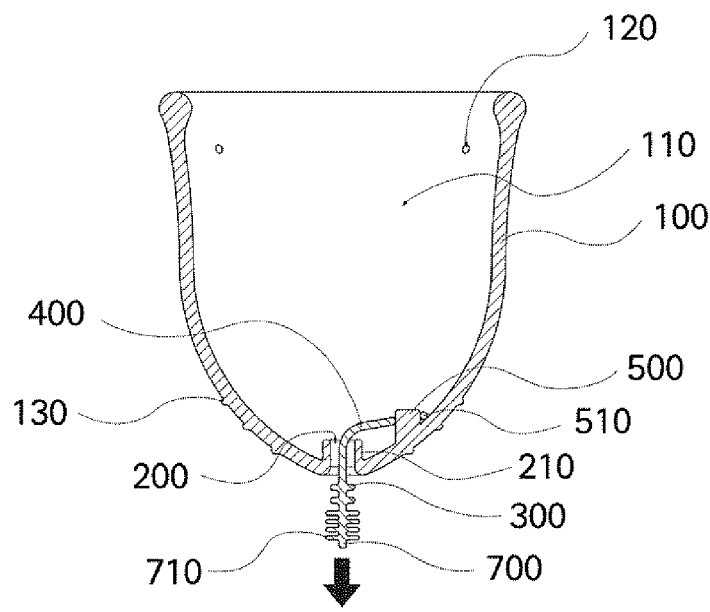
[FIG 22]
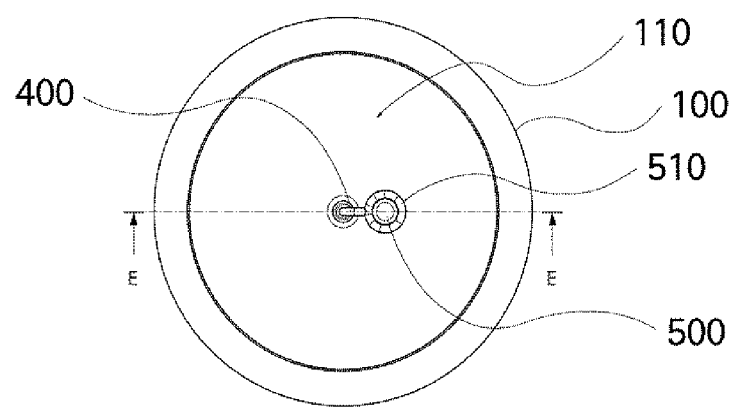

[FIG 23]
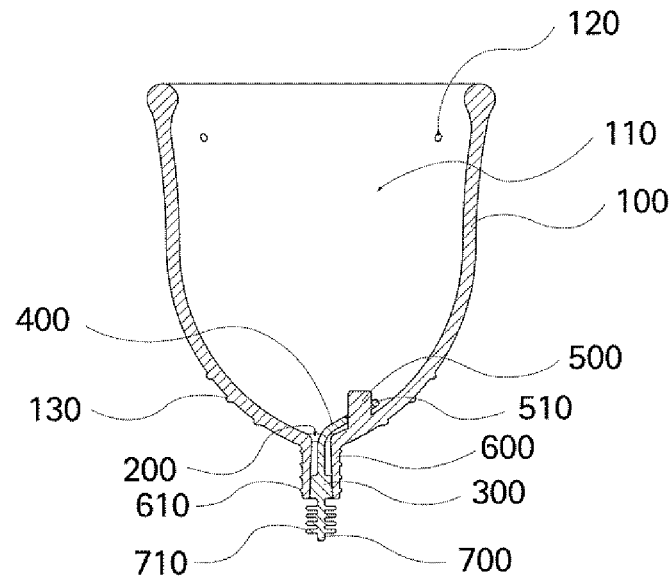
[FIG 24]
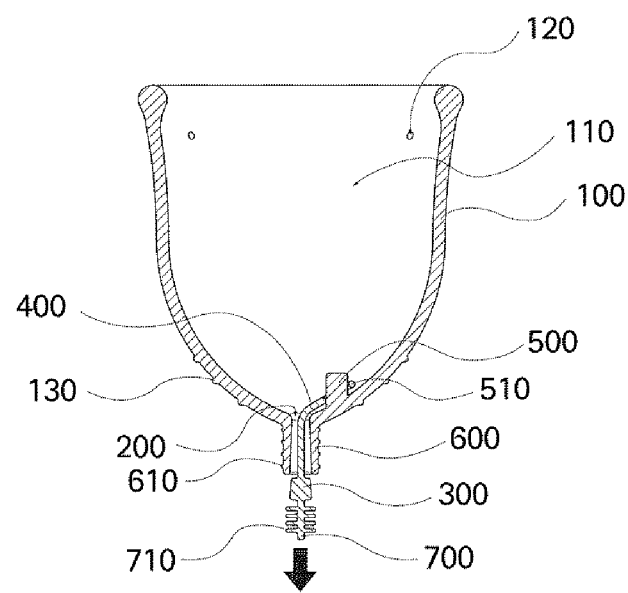

[FIG 25]
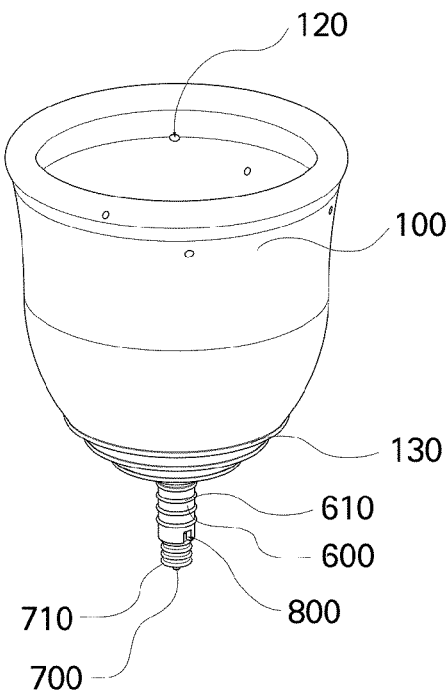
[FIG 26]
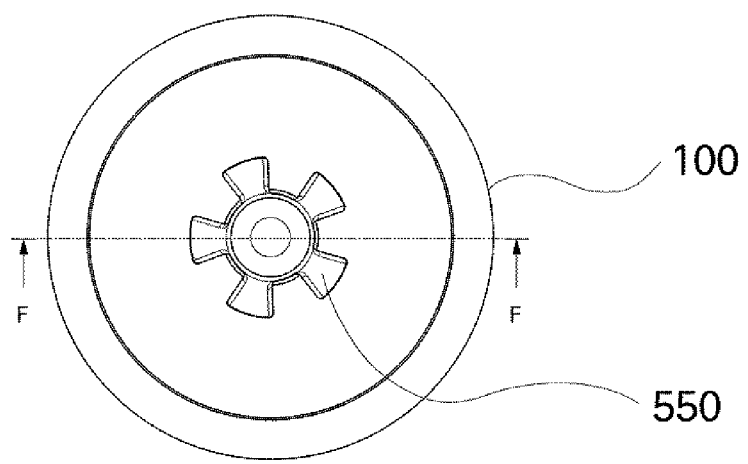

[FIG 27]
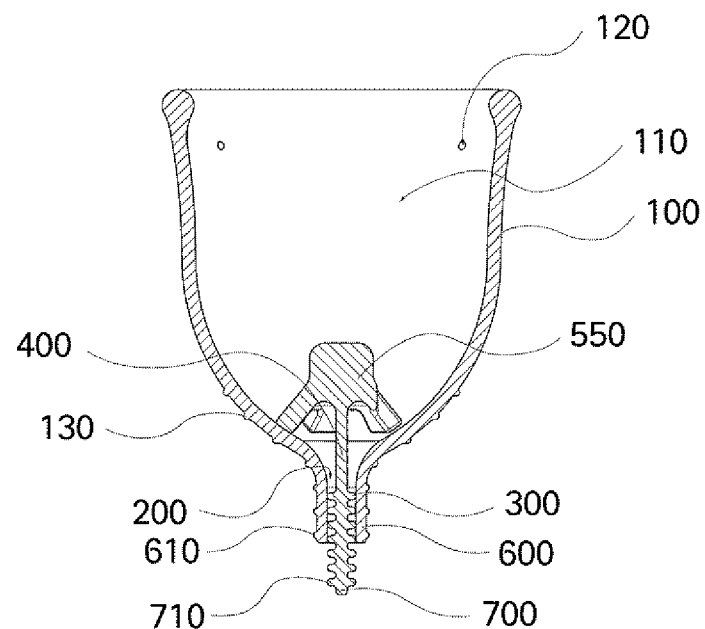
[FIG 28]
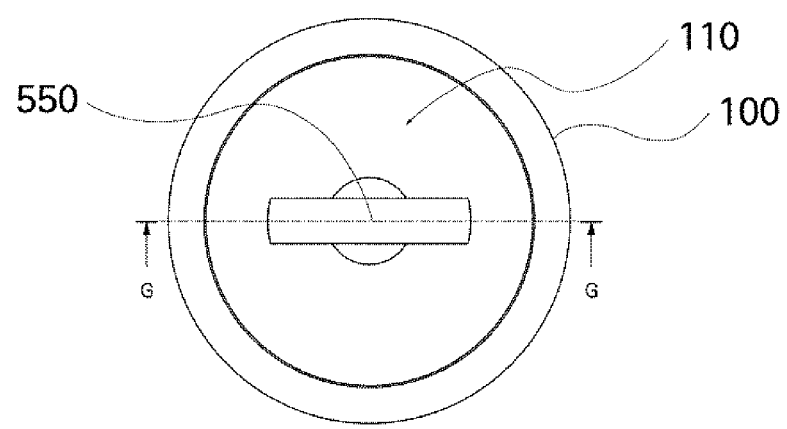

[FIG 29]
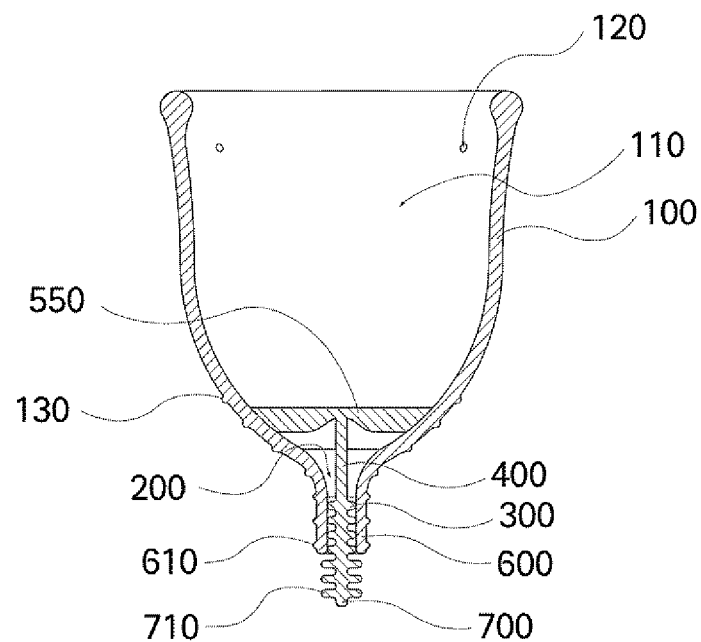
[FIG 30]
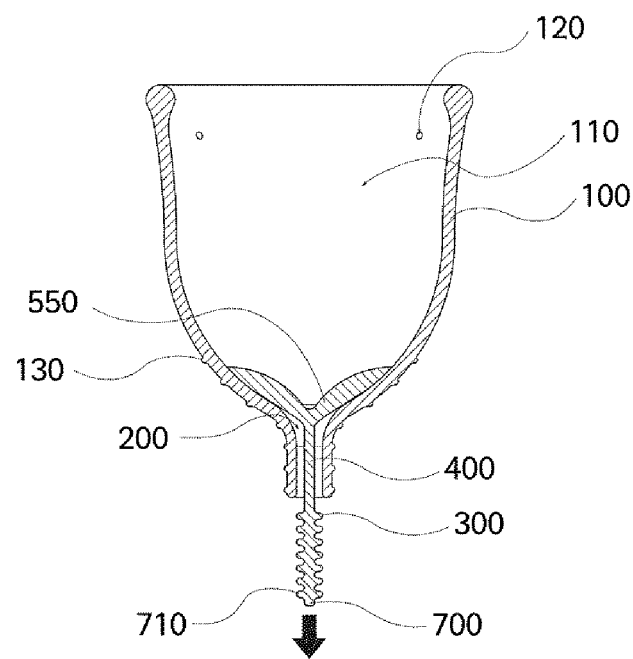

[FIG 31]
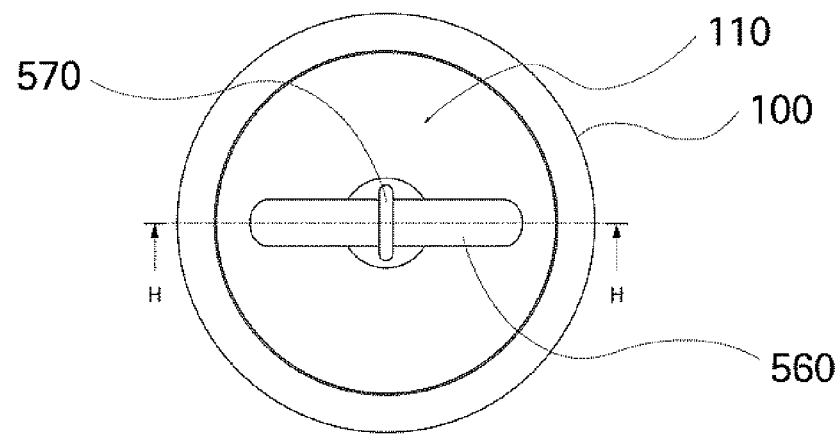
[FIG 32]
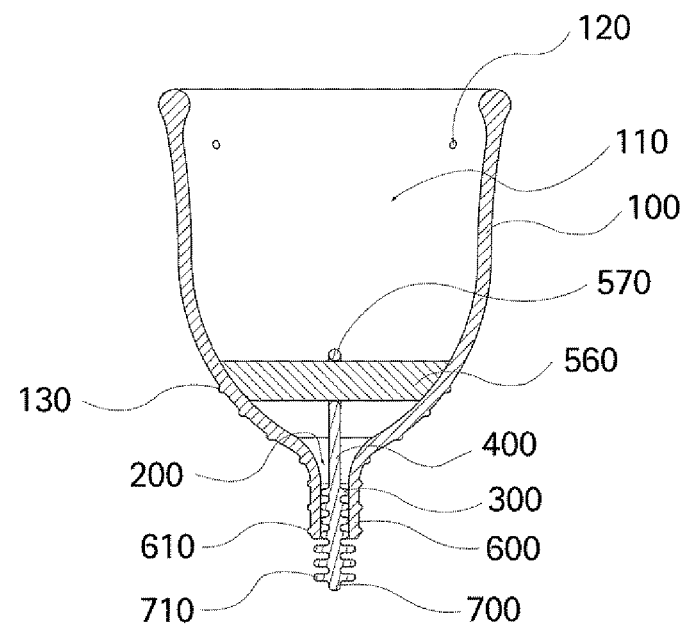

[FIG 33]
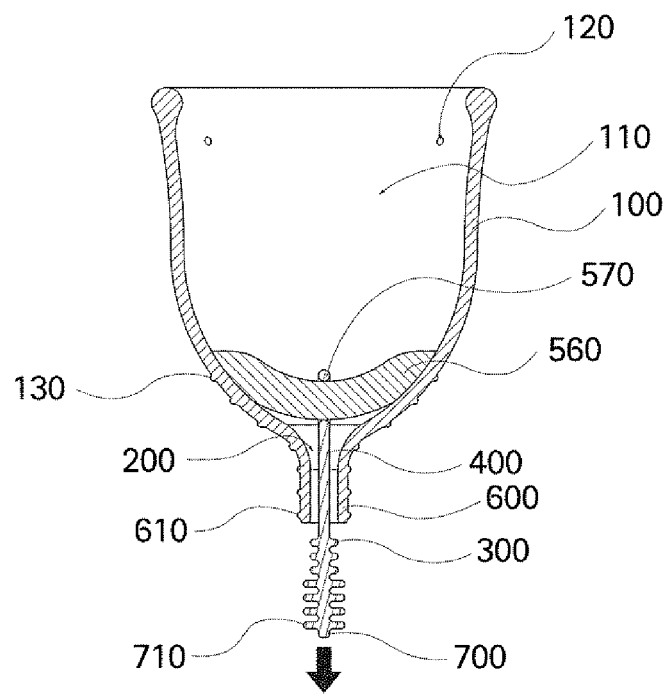
[FIG 34]
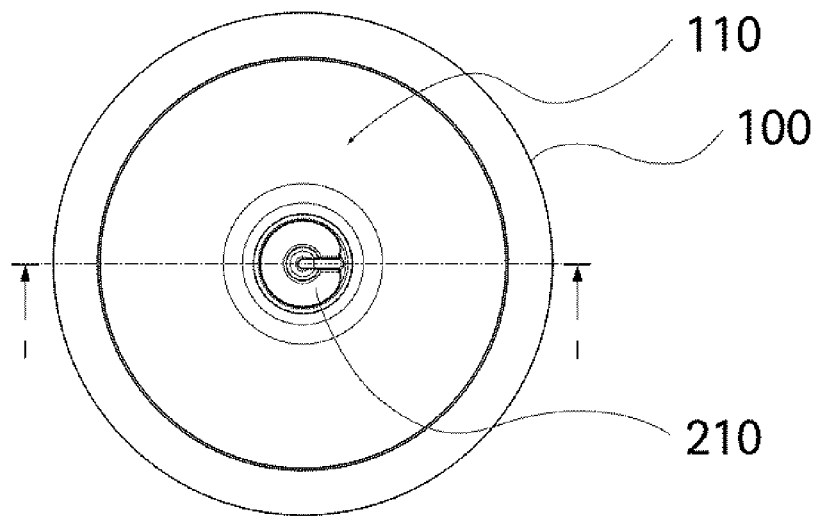

[FIG 35]
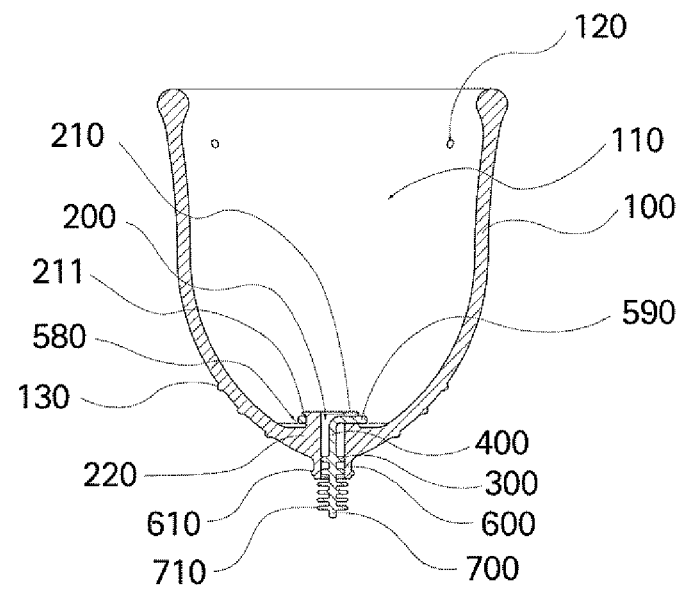
[FIG 36]
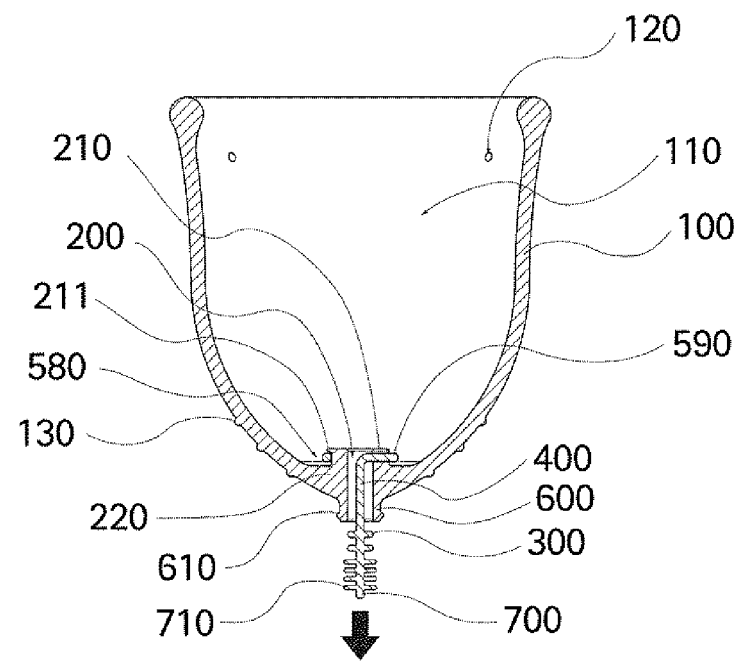

[FIG 37]
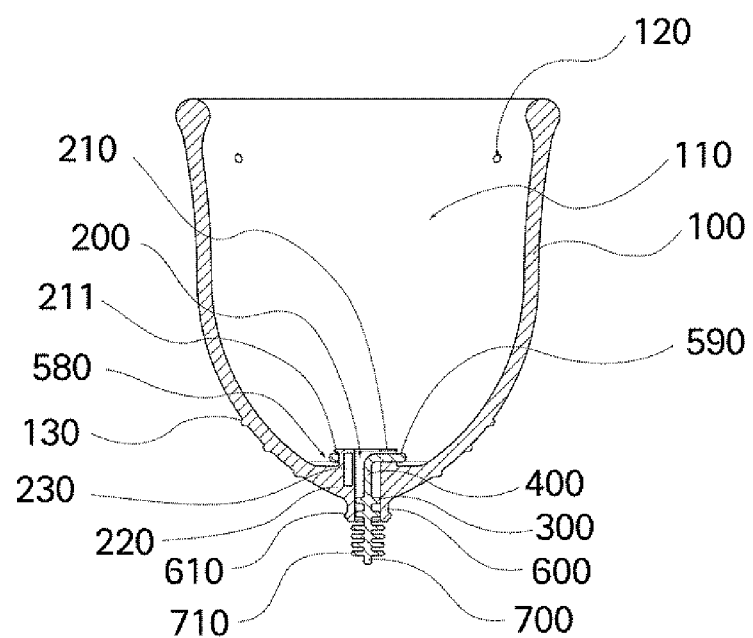

MENSTRUAL CUP

CROSS REFERENCE TO PRIOR APPLICATIONS

This application is the 35 U.S.C. 371 national stage of International application PCT/KR2020/016541 filed on Nov. 23, 2020; which claims priority to Korean Patent Application Nos. 10-2019-0151799 filed on Nov. 25, 2019, 10-2019-0177223 filed on Dec. 30, 2019, 10-2020-0005765 filed on Jan. 16, 2020 and 10-2020-0153237 filed on Nov. 17, 2020. The entire contents of each of the above-identified applications are hereby incorporated by reference.

TECHNICAL FIELD

The present invention relates to a menstrual cup, and more particularly, to an insertional menstrual cup which is inserted into a woman's vagina to accommodate discharged menstrual blood therein.

BACKGROUND ART

Since sanitary napkins and tampons currently used by women are formed of materials such as chemical paper, absorbent nonwoven fabric, and vinyl, an enormous amount of waste occurs. Accordingly, waste disposal costs, pollution occurring in disposal, clogging of drainage and toilet are caused and thus serious water pollution is caused. In addition, expensive products may be a huge financial burden for household. In an aspect of health, it is necessary that plentiful moisture is supplied to a woman's vagina to remove dead cells or bacteria in the vagina. However, conventional sanitary napkins and tampons have a disadvantage of absorbing not only menstrual blood but also moisture.

That is why reusable menstrual cups manufactured using non-toxic silicone are used. However, in the case of menstrual cups, when menstrual blood is collected, a menstrual cup is taken out of a vagina to remove the menstrual blood and is reinserted into the vagina to be used. Accordingly, it is inconvenient to use menstrual cups when going out.

DISCLOSURE

Technical Problem

The present invention is directed to providing a menstrual cup configured to only discharge menstrual blood outward while the menstrual cup is not extracted outward.

The present invention is directed to providing a menstrual cup configured to be easily extracted outward by removing vacuum pressure inside the menstrual cup in advance.

The present invention is directed to providing a menstrual cup configured to be used with a stopper handle or handle of the menstrual cup which is cut to be customized according to a user.

Aspects of the present invention are not limited to the above-stated aspects and other unstated aspects of the present invention will be clearly understood by those skilled in the art from the following description.

Technical Solution

One aspect of the present invention provides a menstrual cup including a body including one open end and a space portion formed therein in which menstrual blood is collected, an outlet disposed in the other end of the body, a stopper packing configured to block the outlet, and a connection portion including one end directly or indirectly connected to the body and the other end connected to the stopper packing so as to allow the stopper packing to be spaced apart from the outlet by an external force and then move the stopper packing to an original position when the external force is removed.

The menstrual cup may further include a catch accommodation portion disposed on the body and a catch portion coupled to the catch accommodation portion and connected to one end of the connection portion.

The menstrual cup may further include a catch portion connected to one end of the connection portion and deformed in a shape when the connection portion is pulled with an external force so as to allow the stopper packing to be spaced apart from the outlet and then move the stopper packing to an original position when the external force is removed.

The menstrual cup may further include a catch portion connected to one end of the connection portion and a catch accommodation portion disposed on the body, coupled to the catch portion, and deformed in a shape when the connection portion is pulled with an external force so as to allow the stopper packing to be spaced apart from the outlet and then move the stopper packing to an original position when the external force is removed.

The menstrual cup may further include a handle protruding outward from the body.

The outlet may pass through an inside of the handle.

The menstrual cup may further include a handle protruding edge which protrudes, in a ring shape, from an outer circumferential surface of the handle.

The menstrual cup may further include a stopper handle connected to the stopper packing and protruding in a direction toward the other end of the stopper packing.

The menstrual cup may further include a stopper handle protruding edge which protrudes, in a ring shape, from an outer circumferential surface of the stopper handle.

An outer circumferential size of the stopper handle protruding edge may be larger than an outer circumferential size of the outlet.

A cross section of the connection portion may be smaller than a cross section of the outlet.

The outlet may become smaller in a direction toward an inside of the body.

The one or more stopper packings may gradually become smaller in a direction toward an inside of the body.

An outer circumferential surface of the stopper packing may become smaller in a direction toward an inside of the body.

A lateral cross-sectional shape of the stopper packing may be equal to a lateral cross-sectional shape of the outlet, and a cross-sectional area of the stopper packing may be larger than a cross-sectional area of the outlet.

The stopper packing may be larger than the outlet so that the outlet may be closed by a pulling force of the connection portion.

The stopper packing may be formed to have a plate shape.

A longitudinal cross section of an outer circumferential surface of the stopper packing may be formed to have a round shape.

Advantageous Effects

According to a menstrual cup of the present invention, one or more effects are present as follows.

According to the present invention, there is an advantage of discharging only menstrual blood outward while a menstrual cup is not extracted outward.

Also, there is an advantage that when a stopper packing is pulled and released after use, the stopper packing moves to an original position to have high usability.

Also, there is an advantage of preventing menstrual blood leakage using a stopper packing.

Also, there is an advantage of easily inserting or removing a stopper packing into or from an outlet because an outer circumferential surface of the stopper packing has a round cross section.

Also, there is an advantage of easily extracting a menstrual cup outward by removing vacuum pressure inside the menstrual cup in advance.

Also, there is an advantage of using a menstrual cup while a stopper handle or handle thereof is cut to be customized according to a user.

Effects of the present invention are not limited to the above-stated effects and other unstated effects of the present invention will be understood by those skilled in the art from the following claims.

DESCRIPTION OF DRAWINGS

FIG. 1 is a plan view of a menstrual cup according to Embodiment 1 of the present invention.

FIG. 2 is a cross-sectional view of the menstrual cup taken along line A-A of FIG. 1 while closed.

FIG. 3 is a cross-sectional view of the menstrual cup taken along line A-A of FIG. 1 while opened.

FIG. 4 is a plan view of a menstrual cup according to Embodiment 2 of the present invention.

FIG. 5 is a cross-sectional view of the menstrual cup taken along line B-B of FIG. 2 while closed.

FIG. 6 is a cross-sectional view of the menstrual cup taken along line B-B of FIG. 2 while opened.

FIG. 7 is a cross-sectional view of a menstrual cup according to Embodiment 3 of the present invention while closed.

FIG. 8 is a cross-sectional view of the menstrual cup according to Embodiment 3 of the present invention while opened.

FIG. 9 is a front view of a menstrual cup according to Embodiment 4 of the present invention while closed.

FIG. 10 is a left side view of the menstrual cup according to Embodiment 4 of the present invention while closed.

FIG. 11 is a front view of the menstrual cup according to Embodiment 4 of the present invention while opened.

FIG. 12 is a perspective view of a menstrual cup according to Embodiment 5 of the present invention while closed.

FIG. 13 is a front view of the menstrual cup according to Embodiment 5 of the present invention while closed.

FIG. 14 is a perspective view of a menstrual cup according to Embodiment 6 of the present invention while closed.

FIG. 15 is a front view of the menstrual cup according to Embodiment 6 of the present invention while opened.

FIG. 16 is a plan view of a menstrual cup according to Embodiment 7 of the present invention.

FIG. 17 is a cross-sectional view of the menstrual cup taken along line C-C of FIG. 16 while closed.

FIG. 18 is a cross-sectional view of the menstrual cup taken along line C-C of FIG. 16 while opened.

FIG. 19 is a plan view of a menstrual cup according to Embodiment 8 of the present invention.

FIG. 20 is a cross-sectional view of the menstrual cup taken along line D-D of FIG. 19 while closed.

FIG. 21 is a cross-sectional view of the menstrual cup taken along line D-D of FIG. 19 while opened.

FIG. 22 is a plan view of a menstrual cup according to Embodiment 9 of the present invention.

FIG. 23 is a cross-sectional view of the menstrual cup taken along line E-E of FIG. 22 while closed.

FIG. 24 is a cross-sectional view of the menstrual cup taken along line E-E of FIG. 22 while opened.

FIG. 25 is a perspective view of a menstrual cup according to Embodiment 10 of the present invention.

FIG. 26 is a plan view of a menstrual cup according to Embodiment 11 of the present invention.

FIG. 27 is a cross-sectional view of the menstrual cup taken along line F-F of FIG. 26 while closed.

FIG. 28 is a plan view of a menstrual cup according to Embodiment 12 of the present invention.

FIG. 29 is a cross-sectional view of the menstrual cup taken along line G-G of FIG. 28 while closed.

FIG. 30 is a cross-sectional view of the menstrual cup taken along line G-G of FIG. 28 while opened.

FIG. 31 is a plan view of a menstrual cup according to Embodiment 13 of the present invention.

FIG. 32 is a cross-sectional view of the menstrual cup taken along line H-H of FIG. 31 while closed.

FIG. 33 is a cross-sectional view of the menstrual cup taken along line H-H of FIG. 31 while opened.

FIG. 34 is a plan view of a menstrual cup according to Embodiment 14 of the present invention.

FIG. 35 is a cross-sectional view of the menstrual cup taken along line I-I of FIG. 34 while closed.

FIG. 36 is a cross-sectional view of the menstrual cup taken along line I-I of FIG. 34 while opened.

FIG. 37 is a cross-sectional view of the menstrual cup of FIG. 35 to which a catch support plate is added.

BEST MODE FOR INVENTION

The advantages and features of the present invention and a method of achieving the same will become apparent with reference to the attached drawings and the following embodiments which will be described below in detail. However, the present invention is not limited to the embodiments which will be described below and may be implemented as a variety of different shapes. It should be noted that the embodiments are provided merely for completing the disclosure of the present invention and allowing one of ordinary skill in the art to completely understand the scope of the present invention and the present invention will be defined by the claims. Throughout the specification, like reference numerals refer to like elements.

Hereinafter, the present invention will be described with reference to the drawings illustrating a menstrual cup according to embodiments of the present invention.

FIG. 1 is a plan view of a menstrual cup according to Embodiment 1 of the present invention, FIG. 2 is a cross-sectional view of the menstrual cup taken along line A-A of FIG. 1 while closed, and FIG. 3 is a cross-sectional view of the menstrual cup taken along line A-A of FIG. 1 while opened.

A body 100 has a cup shape and includes one open end and a space portion 110 formed therein in which menstrual blood is collected.

The body 100 may have a variety of sizes according to a capacity of stored menstrual blood.

An outer circumferential surface of one end of the body 100 may be formed to be greater than an outer circumferential surface of an intermediate portion of the body 100.

When the menstrual cup is inserted into a vagina, the outer circumferential surface of the one end of the body 100 may be pressed against a vagina wall so as to prevent menstrual blood leakage.

Although the outer circumferential surface of the one end of the body 100 is illustrated as a circular shape in the embodiment, unlike this, the outer circumferential surface of the one end of the body 100 has a different shape such as an elliptical shape, a polygonal shape, and the like.

An outlet 200 is formed in a central part of the other end of the body 100, and menstrual blood collected in the space portion 110 is discharged through the outlet 200.

Although the outlet 200 is illustrated as being formed in the other end of the body 100 in the present invention, this position is merely an example and the outlet 200 may be formed in a side surface of the body 100 without departing from a range of purpose of the present invention.

A handle (not shown) may be formed on the other end of the body 100. The handle is formed to extend lengthwise from the other end of the body 100 in a longitudinal direction and allows the body 100 to be easily gripped by a hand when withdrawn from a vagina. Also, the outlet 200 may be formed in the handle.

A stopper packing 300 prevents menstrual blood from being discharged through the outlet 200.

The stopper packing 300 may be larger than the outlet 200.

When the stopper packing 300 is larger than the outlet 200, the outlet 200 may be adequately blocked with the stopper packing 300 so as to further prevent menstrual blood leakage.

A connection portion 400 provides elastic force to allow the stopper packing 300 to return to an original position. The connection portion 400 is connected to one end of the stopper packing 300 and moves the stopper packing 300 to an original position to prevent menstrual blood leakage when an external force is removed after the stopper packing 300 is spaced apart from the outlet 200 due to the external force. The connection portion 400 may be implemented as a variety of components having elasticity such as silicone, rubber, spring, and the like.

One end of the connection portion 400 is connected to an inner surface of the body 100, and the other end of the connection portion 400 is connected to the stopper packing 300.

A stopper handle 700 is connected to the other end of the stopper packing 300. The stopper handle 700 extends lengthwise from the other end of the stopper packing 300 in a longitudinal direction and is configured to allow the stopper packing 300 to be easily gripped by a hand when the stopper packing 300 is spaced apart from the outlet 200.

A stopper handle protruding edge 710 may be a protrusion shape which protrudes, in a ring shape, along an outer circumferential surface of the stopper handle 700.

Since the stopper handle protruding edge 710 is formed on the stopper handle 700, when the stopper handle 700 is pulled, slipping is prevented and grip is improved.

An open hole 120 perforated outward from an inside of the space portion 110 is formed in the outer circumferential surface of the one end of the body 100.

Four open holes 120 may be formed and disposed to be spaced apart along the outer circumferential surface of the one end of the body 100.

The open hole 120 formed in the body 100 becomes a channel through which air flows into the space portion 110 when the body 100 returns to an original shape after being inserted into a vagina.

Also, the open hole 120 performs a function of releasing vacuum pressure. When a part of the body 100 is pushed while the body 100 is inserted into the vagina and thus vacuum pressure is formed between the body 100 and the vagina, outside air flows in through a space formed by pushing the part of the body 100 and the open holes 120 so as to release the vacuum pressure.

A body protruding edge 130 may be a protrusion shape which protrudes, in a ring shape, along an outer circumferential surface of the other end of the body 100.

Since the body protruding edge 130 is formed on the body 100, when the body 100 is pulled, slipping is prevented and grip is improved.

A cross section of the connection portion 400 is smaller than a cross section of the outlet 200.

When a user pulls the stopper packing 300 in a direction away from the body 100 using the stopper handle 700 with an external force, the outlet 200 is opened and thus menstrual blood collected in the space portion 110 is discharged outward through the outlet 200. Here, since the menstrual blood is discharged outward through the outlet 200 when the cross section of the connection portion 400 is smaller than the cross section of the outlet 200, the cross section of the connection portion 400 is necessarily smaller than the cross section of the outlet 200.

The outlet 200 may become smaller from an end of the outlet 200 toward the body 100.

When the outlet 200 is formed to become smaller from the end of the outlet 200 toward the body 100, the intensity of coupling increases as the stopper packing 300 is inserted into the outlet 200. As the intensity of coupling between the outlet 200 and the stopper packing 300 increases, menstrual blood leakage may be further prevented.

Entirely or partially, the menstrual cup may be manufactured using a silicone material which is harmless to a human body.

Although the menstrual cup is illustrated as being entirely or partially formed of silicone in the present invention, the purpose of the present invention is not limited to the material. As an embodiment, the menstrual cup may be entirely or partially manufactured using a variety of materials without departing from the scope of the purpose of the present invention.

The user may cut the stopper handle 700 according to a depth of the user's vagina to use. Since the user feels uncomfortable when the stopper handle 700 is too long, the user may cut the stopper handle 700 according to the depth of the user's vagina to use.

In existing menstrual cups, since it is necessary to take out a menstrual cup from a vagina while a finger is inserted into the vagina and pushes the menstrual cup to release vacuum pressure, there are an inconvenience of inserting the finger into the vagina and a problem that menstrual blood in the menstrual cup partially spills during this process.

When the stopper packing 300 is spaced apart from the outlet 200 using the stopper handle 700 while the menstrual cup is worn on an inside of the vagina, an internal vacuum may be released so as to take out the menstrual cup without causing pain.

In operation according to the embodiment, since the one end of the connection portion 400 is connected to the inner surface of the body 100 and the other end of the connection portion 400 is connected to the stopper packing 300, when the user pulls the stopper packing 300 in a direction away from the body 100 using the stopper handle 700 with an external force, the outlet 200 is opened so that menstrual blood collected in the space portion 110 is discharged outward through the outlet 200.

When the user does not pull the stopper packing 300 in the direction away from the body 100 with the external force, the stopper packing 300 moves to an original position due to the connection portion 400 and thus the outlet 200 is closed so that the menstrual blood collected in the space portion 110 is not discharged outward through the outlet 200.

When the user pulls the stopper packing 300, the stopper handle 700 is connected to the other end of the stopper packing 300 to allow the user to easily pull the stopper packing 300. Also, in order to prevent slipping on the stopper handle 700, the stopper handle protruding edge 710 is formed on the outer circumferential surface of the stopper handle 700.

FIG. 4 is a plan view of a menstrual cup according to Embodiment 2 of the present invention, FIG. 5 is a cross-sectional view of the menstrual cup taken along line B-B of FIG. 2 while closed, and FIG. 6 is a cross-sectional view of the menstrual cup taken along line B-B of FIG. 2 while opened.

Since the body 100, the space portion 110, the open holes 120, the body protruding edge 130, the outlet 200, the stopper packing 300, the connection portion 400, the stopper handle 700, and the stopper handle protruding edge 710 are similar or equal to those described in Embodiment 1, a detailed description will be omitted.

A first catch accommodation portion 500 is disposed on the inner surface of the body 100.

A first catch portion 510 is connected to the one end of the connection portion 400. The first catch portion 510 is coupled to the first catch accommodation portion 500.

The first catch portion 510 is used while being coupled to the fixed first catch accommodation portion 500. The connection portion 400 connected to the first catch portion 510 fixed by the fixed first catch accommodation portion 500 performs a function of moving the stopper packing 300 to an original position when the stopper packing 300 is spaced apart from the outlet 200.

According to Embodiment 2, since the first catch accommodation portion 500 is disposed on the inner surface of the body 100, the first catch portion 510 is connected to the one end of the connection portion 400, and the first catch portion 510 is coupled to the first catch accommodation portion 500, when the user pulls the stopper packing 300 in a direction away from the body 100 using the stopper handle 700 with an external force, the outlet 200 is opened so that menstrual blood collected in the space portion 110 is discharged outward through the outlet 200.

FIG. 7 is a cross-sectional view of a menstrual cup according to Embodiment 3 of the present invention while closed, and FIG. 8 is a cross-sectional view of the menstrual cup according to Embodiment 3 of the present invention while opened.

Since the body 100, the space portion 110, the open holes 120, the body protruding edge 130, the outlet 200, the stopper packing 300, the stopper handle 700, and the stopper handle protruding edge 710 are similar or equal to those described in Embodiment 1, a detailed description will be omitted.

One end of one or more connection portions 400 may be connected to an outer surface of the body 100. Since the one end of one or more connection portions 400 is connected to the body 100, the stopper packing 300 may move to an original position due to an elastic force of the connection portion 400.

One or more connection portions 400 may be arranged to be symmetrical on the basis of the outlet 200 or may be arranged to form uniform intervals or to maintain the balance of power.

According to Embodiment 3, since the one end of the connection portion 400 is connected to the outer surface of the body 100, when the user pulls the stopper packing 300 in a direction away from the body 100 using the stopper handle 700 with an external force, the outlet 200 is opened so that menstrual blood collected in the space portion 110 is discharged outward through the outlet 200.

FIG. 9 is a front view of a menstrual cup according to Embodiment 4 of the present invention while closed, FIG. 10 is a left side view of the menstrual cup according to Embodiment 4 of the present invention while closed, FIG. 11 is a front view of the menstrual cup according to Embodiment 4 of the present invention while opened, FIG. 12 is a perspective view of a menstrual cup according to Embodiment 5 of the present invention while closed, FIG. 13 is a front view of the menstrual cup according to Embodiment 5 of the present invention while closed, FIG. 14 is a perspective view of a menstrual cup according to Embodiment 6 of the present invention while closed, and FIG. 15 is a front view of the menstrual cup according to Embodiment 6 of the present invention while opened.

Since the body 100, the open holes 120, the body protruding edge 130, the stopper packing 300, and the connection portion 400 are similar or equal to those described in Embodiment 1, a detailed description will be omitted.

One or more second catch accommodation portions 520 may be disposed on an outer surface of the body 100. The second catch accommodation portions 520 may be connected to the outer surface of the body 100 or disposed to be engraved therein.

One or more second catch portions 530 are connected to one end of the connection portion 400.

The second catch portions 530 are connected to the connection portion 400 and coupled to the second catch accommodation portions 520 so that the stopper packing 300 may move to an original position due to an elastic force of the connection portion 400.

One or more second catch accommodation portions 520 may be arranged to be symmetrical on the basis of the outlet 200 or may be arranged to form uniform intervals or to maintain the balance of power.

Like Embodiment 6, one second catch accommodation portion (not shown) may be formed on the outer surface of the body 100 and one or more second catch portions 530 may be formed on one end of the connection portion 400.

The second catch accommodation portion may be formed to be engraved in an outer surface of a handle (not shown) or the body 100.

The second catch accommodation portion may be formed on the outer surface of the body 100 and one or more second catch portions 530 may be formed on the connection portion 400 so that the second catch portion 530 may be coupled to the second catch accommodation portion. Accordingly, the stopper packing 300 may move to an original position due to an elastic force of the connection portion 400.

According to Embodiments 4 to 6, since one or more second catch accommodation portions 520 are disposed on the body 100 and one or more second catch portions 530 are connected to one end of the connection portion 400, when the user pulls the stopper packing 300 in a direction away from the body 100 with an external force, the outlet 200 is opened so that menstrual blood collected in the space portion 110 is discharged outward through the outlet 200.

FIG. 16 is a plan view of a menstrual cup according to Embodiment 7 of the present invention, FIG. 17 is a cross-sectional view of the menstrual cup taken along line C-C of FIG. 16 while closed, and FIG. 18 is a cross-sectional view of the menstrual cup taken along line C-C of FIG. 16 while opened.

Since the body 100, the space portion 110, the open holes 120, the body protruding edge 130, the connection portion 400, the first catch accommodation portion 500, the first catch portion 510, and the stopper handle 700 are similar or equal to those described in Embodiment 1 or 2, a detailed description will be omitted.

The stopper handle protruding edge 710 may be formed to be greater than the outlet 200. Since the stopper handle protruding edge 710 is formed to be greater than the outlet 200, when a user pulls the stopper packing 300 in a direction away from the body 100 with an external force and releases the stopper packing 300, the stopper handle 700 is prevented from being inserted into the outlet 200 due to elasticity.

A handle 600 may have a shape protruding outward from the body 100. The handle 600 may be disposed on the other end of the body 100. The handle 600 is formed to extend lengthwise from the other end of the body 100 in a longitudinal direction so as to allow the body 100 to be easily gripped and taken out by a hand while being withdrawn from a vagina.

The outlet 200 is formed in the handle 600. The outlet 200 may pass through the handle 600.

The outlet 200 is formed in a central part of the handle 600 so that menstrual blood collected in the space portion 110 is discharged through the outlet 200.

A handle protruding edge 610 is disposed on an outer circumferential surface of the handle 600.

The handle protruding edge 610 is a protrusion protruding, in a ring shape, along the outer circumferential surface of the handle 600. Since the handle protruding edge 610 is formed on the handle 600, when the handle 600 is pulled, slipping is prevented and grip is improved.

The user may cut the handle 600 according to a depth of the user's vagina to use. Since the user feels uncomfortable when the handle 600 is too long, the user may cut the handle 600 according to the depth of the user's vagina to use.

When the handle 600 is cut to be used, the connection portion 400 is used while being cut by a part as much as a cut part of the handle 600 or replaced with a shorter connection portion 400. Alternatively, one or more first catch portions 510 may be disposed so as to be used while being cut as much as the cut part of the handle 600.

A lateral cross-sectional shape of the stopper packing 300 may be equal to a lateral cross-sectional shape of the outlet 200, and a cross-sectional area of the stopper packing 300 may be larger than or equal to a cross-sectional area of the outlet 200.

When the lateral cross-sectional shape of the stopper packing 300 is necessarily equal to the lateral cross-sectional shape of the outlet 200 and the cross-sectional area of the stopper packing 300 is necessarily larger than or equal to the cross-sectional area of the outlet 200, menstrual blood collected in the space portion 110 is not discharged outward through the outlet 200. Although the lateral cross-sectional shape of the outlet 200 and the lateral cross-sectional shape of the stopper packing 300 are illustrated as being formed to be a circular shape in the embodiment, unlike this, other shapes such as an elliptical shape, polygonal shape, and the like are applicable thereto.

The stopper packing 300 may be formed to have a plate shape to be easily inserted into and removed from the outlet 200.

A longitudinal cross section of an outer circumferential surface of the stopper packing 300 may be formed to be a round shape. When the longitudinal cross section of the outer circumferential surface of the stopper packing 300 is a round shape, the stopper packing 300 is easily insertable into and removable from the outlet 200 and may stably block the outlet 200.

The outlet 200 becomes smaller in a direction toward the body 100. When the outlet 200 is formed to become smaller in the direction toward the body 100, the intensity of coupling increases as the stopper packing 300 is inserted into the outlet 200. As the intensity of coupling between the outlet 200 and the stopper packing 300 increases, menstrual blood leakage may be further prevented.

One or more stopper packings 300 may be formed. When one or more stopper packings 300 are formed, the stopper packing 300 may further stably block the outlet 200.

The one or more stopper packings 300 may gradually become smaller in a direction toward an inside of the body 100. When the one or more stopper packings 300 are formed to gradually become smaller in the direction toward the inside of the body 100, the stopper packing 300 is easily insertable into the outlet 200 and the intensity of coupling increases as the stopper packings 300 are inserted into the outlet 200. As the intensity of coupling between the outlet 200 and the stopper packings 300 increases, menstrual blood leakage may be further prevented.

According to Embodiment 7, since the first catch accommodation portion 500 is disposed on the inner surface of the body 100, the first catch portion 510 is connected to the one end of the connection portion 400, and the first catch portion 510 is coupled to the first catch accommodation portion 500, when the user pulls the stopper packings 300 in a direction away from the body 100 using the stopper handle 700 with an external force, the outlet 200 is opened so that menstrual blood collected in the space portion 110 is discharged outward through the outlet 200.

FIG. 19 is a plan view of a menstrual cup according to Embodiment 8 of the present invention, FIG. 20 is a cross-sectional view of the menstrual cup taken along line D-D of FIG. 19 while closed, and FIG. 21 is a cross-sectional view of the menstrual cup taken along line D-D of FIG. 19 while opened.

Since the body 100, the space portion 110, the open holes 120, the body protruding edge 130, the outlet 200, the stopper packing 300, the connection portion 400, the first catch accommodation portion 500, the first catch portion 510, the stopper handle 700, and the stopper handle protruding edge 710 are similar or equal to those described in Embodiments 1, 2, and 7, a detailed description will be omitted.

A discharge tube 210 is formed lengthwise in a direction from the other end to one end of the body 100.

The discharge tube 210 may allow a length of the outlet 200 to be increased.

When the discharge tube 210 is formed lengthwise, the outlet 200 formed in the discharge tube 210 may also be formed to be long. When the outlet 200 is formed lengthwise, the stopper packing 300 may better block the outlet 200 so as to further prevent menstrual blood leakage.

FIG. 22 is a plan view of a menstrual cup according to Embodiment 9 of the present invention, FIG. 23 is a cross-sectional view of the menstrual cup taken along line E-E of FIG. 22 while closed, and FIG. 24 is a cross-sectional view of the menstrual cup taken along line E-E of FIG. 22 while opened.

Since the body 100, the space portion 110, the open holes 120, the body protruding edge 130, the outlet 200, the stopper packing 300, the connection portion 400, the first catch accommodation portion 500, the first catch portion 510, the handle 600, the handle protruding edge 610, the stopper handle 700, and the stopper handle protruding edge 710 are similar or equal to those described in Embodiments 1, 2, and 7, a detailed description will be omitted.

An outer circumferential surface of the stopper packing 300 becomes smaller in a direction toward an inside of the body 100. When the outer circumferential surface of the stopper packing 300 is formed to become smaller in the direction toward the inside of the body 100, the intensity of coupling increases as the stopper packing 300 is inserted into the outlet 200. As the intensity of coupling between the outlet 200 and the stopper packing 300 increases, menstrual blood leakage may be further prevented.

FIG. 25 is a perspective view of a menstrual cup according to Embodiment of the present invention.

Since the body 100, the space portion (not shown), the open holes 120, the body protruding edge 130, the outlet (not shown), the stopper packing (not shown), the connection portion (not shown), the first catch accommodation portion (not shown), the first catch portion (not shown), the handle 600, the handle protruding edge 610, the stopper handle 700, and the stopper handle protruding edge 710 are similar or equal to those described in Embodiments 1, 2, and 7, a detailed description will be omitted.

A stopper packing catch portion 800 is formed on one end of the handle 600. The stopper packing catch portion 800 is used so that the stopper packing 300 is caught on and fixed to the stopper packing catch portion 800 after a user pulls the stopper packing 300 in a direction away from the body 100 with an external force.

Since the stopper packing 300 is fixed, while menstrual blood is discharged outward through the outlet 200, the stopper packing 300 may be easily fixed.

FIG. 26 is a plan view of a menstrual cup according to Embodiment 11 of the present invention, FIG. 27 is a cross-sectional view of the menstrual cup taken along line F-F of FIG. 26 while closed, FIG. 28 is a plan view of a menstrual cup according to Embodiment 12 of the present invention, FIG. 29 is a cross-sectional view of the menstrual cup taken along line G-G of FIG. 28 while closed, and FIG. 30 is a cross-sectional view of the menstrual cup taken along line G-G of FIG. 28 while opened.

Since the body 100, the space portion 110, the open holes 120, the body protruding edge 130, the outlet 200, the stopper packing 300, the connection portion 400, the handle 600, the handle protruding edge 610, the stopper handle 700, and the stopper handle protruding edge 710 are similar or equal to those described in Embodiments 1 and 7, a detailed description will be omitted.

A third catch portion 550 is connected to one end of the connection portion 400. When the connection portion 400 is pulled with an external force, a shape of the third catch portion 550 is deformed so that the stopper packing 300 is spaced apart from the outlet 200. Here, when the external force is removed, the shape of the third catch portion 550 may be restored so as to move the stopper packing 300 to an original position.

In operation according to the embodiment, since the third catch portion 550 is connected to one end of the connection portion 400, when the user pulls the stopper packing 300 in a direction away from the body 100 using the stopper handle 700 with an external force, the outlet 200 is opened so that menstrual blood collected in the space portion 110 is discharged outward through the outlet 200.

Since the third catch portion 550 provides an elastic force to move to an original position, when the user pulls the stopper packing 300 in the direction away from the body 100 using the stopper handle 700 with an external force, the third catch portion 550 bends in the direction away from the body 100 and thus the outlet 200 is opened so that the menstrual blood collected in the space portion 110 is discharged outward through the outlet 200. When the user does not pull the stopper packing 300 in the direction away from the body 100 with the external force, the third catch portion 550 moves to an original position due to an elastic force and the stopper packing 300 moves to an original position due to the connection portion 400 connected to the third catch portion 550 and thus the outlet 200 is closed so that the menstrual blood collected in the space portion 110 is not discharged outward through the outlet 200.

FIG. 31 is a plan view of a menstrual cup according to Embodiment 13 of the present invention, FIG. 32 is a cross-sectional view of the menstrual cup taken along line H-H of FIG. 31 while closed, and FIG. 33 is a cross-sectional view of the menstrual cup taken along line H-H of FIG. 31 while opened.

Since the body 100, the space portion 110, the open holes 120, the body protruding edge 130, the outlet 200, the stopper packing 300, the connection portion 400, the handle 600, the handle protruding edge 610, the stopper handle 700, and the stopper handle protruding edge 710 are similar or equal to those described in Embodiments 1 and 7, a detailed description will be omitted.

A fourth catch portion 570 is connected to one end of the connection portion 400. A fourth catch accommodation portion 560 is disposed on the body 100. The fourth catch accommodation portion 560 is coupled to the fourth catch portion 570. When the connection portion 400 is pulled with an external force, a shape of the fourth catch accommodation portion 560 is deformed so that the stopper packing 300 is spaced apart from the outlet 200. Here, when the external force is removed, the shape of the fourth catch accommodation portion 560 may be restored so as to move the stopper packing 300 to an original position.

In operation according to the embodiment, since the fourth catch portion 570 is connected to one end of the connection portion 400 and coupled to the fourth catch accommodation portion 560 and the fourth catch accommodation portion 560 is disposed on the body 100, when the user pulls the stopper packing 300 in a direction away from the body 100 using the stopper handle 700 with an external force, the outlet 200 is opened so that menstrual blood collected in the space portion 110 is discharged outward through the outlet 200.

The fourth catch accommodation portion 560 may provide an elastic force to move to an original position. When the user pulls the stopper packing 300 in the direction away from the body 100 using the stopper handle 700 with an external force, the fourth catch accommodation portion 560 bends in the direction away from the body 100, and thus the outlet 200 is opened so that the menstrual blood collected in the space portion 110 may be discharged outward through the outlet 200. When the user does not pull the stopper packing 300 in the direction away from the body 100 with the external force, the fourth catch accommodation portion 560 changes to an original shape due to the elastic force and the stopper packing 300 moves to an original position due to the connection portion 400 connected to the fourth catch accommodation portion 560 and thus the outlet 200 is closed so that the menstrual blood collected in the space portion 110 is not discharged outward through the outlet 200.

FIG. 34 is a plan view of a menstrual cup according to Embodiment 14 of the present invention, FIG. 35 is a cross-sectional view of the menstrual cup taken along line I-I of FIG. 34 while closed, FIG. 36 is a cross-sectional view of the menstrual cup taken along line I-I of FIG. 34 while opened, and FIG. 37 is a cross-sectional view of the menstrual cup of FIG. 35 to which a catch support plate is added.

Since the body 100, the space portion 110, the open holes 120, the body protruding edge 130, the outlet 200, the discharge tube 210, the stopper packing 300, the connection portion 400, the handle 600, the handle protruding edge 610, the stopper handle 700, and the stopper handle protruding edge 710 are similar or equal to those described in Embodiments 1, 7, and 8, a detailed description will be omitted.

A discharge tube support portion 220 is disposed between the discharge tube 210 and the body 100.

A discharge tube support plate 230 is disposed on an inner or outer surface of the discharge tube 210.

A fifth catch accommodation portion 580 is disposed on an outer surface of one end of the discharge tube 210.

A discharge tube step 211 is disposed on an outer surface of the one end of the discharge tube 210.

A fifth catch portion 590 is connected to one end of the connection portion 400. The fifth catch portion 590 is coupled to the fifth catch accommodation portion 580.

To prevent a part of the discharge tube 210 from being bent by the connection portion 400 connected to the stopper packing 300 when the stopper packing 300 is pulled in a direction away from the body 100, one side surface of the discharge tube 210 may be cut so as to form a space through which the connection portion 400 may pass.

The discharge tube 210 may be manufactured to have a thickness so that the part of the discharge tube 210 is not bent by the connection portion 400 connected to the stopper packing 300 when the stopper packing 300 is pulled in the direction away from the body 100.

The discharge tube step 211 prevents the fifth catch portion 590 connected to the connection portion 400 connected to the stopper packing 300 from being released from the fifth catch accommodation portion 580 when the stopper packing 300 is pulled in the direction away from the body 100.

The discharge tube support portion 220 supports the discharge tube 210 when the stopper packing 300 is pulled in the direction away from the body 100.

The discharge tube support plate 230 supports the discharge tube 210 not to be bent when the stopper packing 300 is pulled in the direction away from the body 100.

According to Embodiment 14, since the fifth catch accommodation portion 580 is formed on the outer surface of the one end of the discharge tube 210, the fifth catch portion 590 is connected to the one end of the connection portion 400, and the fifth catch portion 590 is coupled to the fifth catch accommodation portion 580, when the user pulls the stopper packing 300 in a direction away from the body 100 using the stopper handle 700 with an external force, the outlet 200 is opened so that menstrual blood collected in the space portion 110 is discharged outward through the outlet 200.

Although the exemplary embodiments of the present invention have been illustrated and described above, the present invention is not limited to the above particularly embodiments. Also, it should be noted that a variety of modifications may be made by one of ordinary skill in the art without departing from the essential of the present invention which is claimed by the following claims and the modifications are not separately understood from the technical concept or vision of the present invention.

The invention claimed is:

1. A menstrual cup comprising:
   a body including one open end and a space portion formed therein in which menstrual blood is collected;
   an outlet disposed in the other end of the body;
   a stopper packing configured to block the outlet;
   a connection portion including one end directly or indirectly connected to the body and the other end connected to the stopper packing so as to allow the stopper packing to be spaced apart from the outlet by an external force and then move the stopper packing to an original position when the external force is removed;
   a catch accommodation portion disposed on the body; and
   a catch portion coupled to the catch accommodation portion and connected to one end of the connection portion.

2. The menstrual cup of claim 1, further comprising a handle protruding outward from the body.

3. The menstrual cup of claim 2, wherein the outlet passes through an inside of the handle.

4. The menstrual cup of claim 2, further comprising a handle protruding edge which protrudes, in a ring shape, from an outer circumferential surface of the handle.

5. The menstrual cup of claim 1, further comprising a stopper handle connected to the stopper packing and protruding in a direction toward the other end of the stopper packing.

6. The menstrual cup of claim 5, further comprising a stopper handle protruding edge which protrudes, in a ring shape, from an outer circumferential surface of the stopper handle.

7. The menstrual cup of claim 6, wherein an outer circumferential size of the stopper handle protruding edge is larger than an outer circumferential size of the outlet.

8. The menstrual cup according to claim 1, wherein a cross section of the connection portion is smaller than a cross section of the outlet.

9. A menstrual cup comprising:
   a body including one open end and a space portion formed therein in which menstrual blood is collected;
   an outlet disposed in the other end of the body;
   a stopper packing configured to block the outlet;
   a connection portion including one end directly or indirectly connected to the body and the other end connected to the stopper packing so as to allow the stopper packing to be spaced apart from the outlet by an external force and then move the stopper packing to an original position when the external force is removed; and
   a catch portion connected to one end of the connection portion and deformed in a shape when the connection portion is pulled with an external force so as to allow the stopper packing to be spaced apart from the outlet and then move the stopper packing to an original position when the external force is removed.

10. A menstrual cup comprising:
    a body including one open end and a space portion formed therein in which menstrual blood is collected;
    an outlet disposed in the other end of the body;
    a stopper packing configured to block the outlet;
    a connection portion including one end directly or indirectly connected to the body and the other end connected to the stopper packing so as to allow the stopper packing to be spaced apart from the outlet by an external force and then move the stopper packing to an original position when the external force is removed;

a catch portion connected to one end of the connection portion; and a catch accommodation portion disposed on the body, coupled to the catch portion, and deformed in a shape when the connection portion is pulled with an external force so as to allow the stopper packing to be spaced apart from the outlet and then move the stopper packing to an original position when the external force is removed.

* * * * *